United States Patent [19]

Feinberg et al.

[11] Patent Number: 5,240,840
[45] Date of Patent: Aug. 31, 1993

[54] DNA SUPERFRAGMENT CLONING

[75] Inventors: Andrew P. Feinberg, Ann Arbor; Minoru Koi, Ypsilanti, both of Mich.

[73] Assignee: Regents of the University of Michigan, Ann Arbor, Mich.

[21] Appl. No.: 680,766

[22] Filed: Apr. 5, 1991

[51] Int. Cl.$^5$ .................. C12N 15/10; C12N 15/11; C12N 15/12
[52] U.S. Cl. .................. 435/172.3; 435/91; 536/23.1; 536/23.5
[58] Field of Search .............. 435/172.1, 172.3, 320.1, 435/91; 536/27, 23.1, 23.5

[56] References Cited

PUBLICATIONS

Goss et al. (Jun. 26, 1975), Nature, vol. 255, pp. 680–684.
Leach et al. (Aug. 1989), Genomics, vol. 5, pp. 167–176.
Reeve et al. (Apr. 1989), Mol. Cell. Biol., vol. 9(4), pp. 1799–1803.
Somnatic Cell and Molecular Genetics, vol. 16, No. 5, pp. 425–435, Sep., 1990, T. S. Siden, et al., "Monochromosomal Mouse Microcell Hybrids Containing Inserted Selectable Neo Genes".

*Primary Examiner*—Richard A. Schwartz
*Assistant Examiner*—Philip W. Carter
*Attorney, Agent, or Firm*—Oblon, Spivak, McClelland, Maier & Neustadt

[57] ABSTRACT

Superfragments of chromosomal DNA having 1 million to 100 million base pairs may be formed by irradiating microcells containing a chromosome with a high dose of $\gamma$-irradiation. Such superfragments are useful for the rapid cloning of genes.

6 Claims, 6 Drawing Sheets

DNA SUPERFRAGMENT CLONING

BACKGROUND OF THE INVENTION

1. Field of the Invention

The present invention relates to DNA superfragments, a method of preparing DNA superfragments, and a method of cloning which utilizes DNA superfragments.

2. Discussion of the Background

The primary goal of most genetic laboratories is to identify, isolate (clone) and characterize genes. This primary function is severely hampered in eukaryotes by the complexity (size) of the genome (e.g., the human genome contains $3 \times 10^9$ base pairs on each set of chromosomes), and by the fact that transcribed (functioning) genes represent only a small percentage of the genetic material, which is hidden among the remaining DNA. While great progress has been made in the isolation of genes involved in metabolic pathways, because of the abundance of the proteins encoded by such genes and the availability of biochemical selection for the property of the gene product (i.e., assays that allow the elimination of cells that do not contain the desired gene product), cloning of most genes currently requires more tedious "reverse genetics" approaches.

These approaches rely on the localization of a gene to a particular chromosome or chromosomal region, and then "walking" along a chromosome from a known DNA marker to the desired gene. There are several problems inherent in reverse genetic approaches. These include but ar not limited to the following:

(i) Currently, if one knows the approximate chromosomal location of a gene, one can look for the nearest chromosomal marker and then walk along the chromosome to the gene (*Molecular Cloning, A Laboratory Manual,* 2nd Ed., J. Sanbrook, E.F. Fritsch, and T. Maniatis, Cold Spring Harbor Laboratory Press (1989)). There are 3 billion base pairs of DNA along the length of the genome. Typically, available DNA markers are sparsely distributed (H. Donis-Keller et al, "A Genetic Linkage Map of the Human Genome", *Cell,* vol. 51, pp. 319-337 (1987)). For example, only seven markers have been mapped over a range of 15 centimorgans (approximately 15 million base pairs) in a region of chromosomal band 11p15 that may harbor a tumor suppressor gene. Worse, these markers are often not equally spaced and there are often large regions that lack DNA markers. In order to walk from one chromosomal location to another, one uses a DNA marker or probe to screen a genomic library containing the entire human genome or a large portion of the chromosome of interest. One identifies clones that contain this marker. A typical bacteriophage library contains DNA fragments of approximately 15,000 base pairs. Thus, each chromosomal walk will allow isolation of new fragments at an average distance of 15,000 base pairs A total of over 60 such walks (at best requiring 1 month each) is necessary to walk each one million base pairs. Specialized methods have been developed to shorten this process. The most successful of these approaches, yeast artificial chromosome cloning (Burke, D. T.; Carle, G. F.; and Olson, M. V., *Science,* vol. 236, pp. 806-812, (1987)), allows one to walk through a library, in increments of approximately 250,000 base pairs on average. In the example of chromosome 11, this process would still require over 500 YACs to encompass the chromosome, but several times that number to account for overlap. Furthermore, one may walk for quite a distance and then get "stuck", if there is a gap in the representation of the library, which often occurs.

(ii) One often does not know which of many transcribed sequences in a walking effort represents the gene of interest, since there is no convenient way to assay for the gene's properties. This is because in conventional reverse genetic approaches, only a portion of the gene is isolated and considerable additional effort is necessary to obtain a functionally useful clone. This requires a second effort of cloning, in this case using probes derived from genomic walking to screen a cDNA library. The entire cDNA must be isolated, which is often difficult, and it must be placed into the appropriate expression vector in order to assay for the phenotypic properties of its expression. Because of this, complementation studies (screening tests demonstrating the functional properties of the gene) commonly are done later than gene cloning, and they are not helpful in actually isolating the gene. The identity of the gene is thus usually confirmed by identification of mutations within candidate genes in disease states (Riordan, Jr. et al, "Identification of the cystc fibrosis gene: cloning and characterization of complementary DNA", *Science,* vol. 245, pp. 1066-1073 (1989)), association with chromosomal alterations (Friend et al, "A Human DNA Segment with Properties of the Gene that Predisposes to Retinoblastoma and Osteosarcoma", Nature, vol. 323, pp. 643-646 (1986)), or other cumbersome means. Since one often does not know the precise location of the gene of interest and must begin with a candidate region of millions of base pairs or even a whole chromosomal arm or entire chromosome, there is often no clear starting point and no well-defined endpoint.

(iii) Current strategies do not permit one to screen clones for the biological property that the gene of interest confers. For the purposes of the present application, a screening process is any process, by which it is possible to determine if a cell expresses a particular gene product, which is not based on the selective survival of the cell or the ability to isolate the cell from all other cells because of the expression of the particular gene product. In contrast, for the purposes of the present application, a selection process is any process, by which it is possible to determine if a cell expresses a particular gene product, which is based on the selective survival of the cell or the ability to isolate the cell from all other cells because of the expression of the particular gene product. Thus, there is currently no generalized strategy that would allow one to screen for a gene, enabling one to know which of many clones contain the gene with the properties one desires, unless there is a way to select for that gene as well. This is a common problem in molecular biology. One can easily design a "library" of tens of thousands of genes, each in a bacterial colony, but unless one has a way of selecting those colonies that express the gene of interest, one cannot find the "needle in a haystack", namely the colony containing the gene of interest among the many thousands of other genes.

For example, one can screen for a cell containing a tumor suppressor gene, because the growth of that cell is inhibited by the gene. However, one cannot select for such a cell, because by definition, cells containing this gene will grow more slowly than cells not containing the gene, and thus selection strategies will select against the gene of interest. There have been several failed efforts to circumvent this problem, and current cloning strategies for tumor suppressor genes rely on reverse genetic methods, i.e., they do not depend upon a screening test for the gene.

Other examples of genes for which screening is possible but selection is not include the following:

(a) Genes that cause chromosomal breakage. There are several human clinical disorders that predispose one to chromosomal breakage, birth defects, and cancer. Indeed, one of these, ataxia talagiectasia, is thought to account for as much as 15% of the incidences of breast cancer in the general population.

(b) Very large genes that are difficult to transfer intact using conventional vectors such as a phage or cosmid.

(c) Genes which encode integral membrane proteins or receptors that are difficult to purify.

(d) Genes which cause cellular aging.

(e) Trans-acting genes that regulate, directly or indirectly, other genes.

Thus, there remains a need for a method of cloning genes which is free of the above-mentioned drawbacks. In particular, there remains a need for a method of cloning genes for which there is no method of selection, such as tumor suppresor genes, genes that cause chromosomal breakage, very large genes, genes which cause cellular aging, and encode integral membrane proteins or receptors that are difficult to purify, and transacting genes.

SUMMARY OF THE INVENTION

Accordingly, it is one object of the present invention to provide a method for cloning genes.

It is another object of the present invention to provide a method for cloning genes for which there is no method of selection.

It is another object of the present invention to provide a method for cloning tumor suppressor genes.

It is another object of the present invention to provide DNA fragments which facilitate the present method.

It is another object of the present invention to provide DNA fragments which contain genes for which there is no method of selection.

It is another object of the present invention to provide DNA fragments which contain a tumor suppressor gene.

It is another object of the present invention to provide a method for preparing DNA fragments which facilitate the present method.

It is another object of the present invention to provide a method for preparing DNA fragments which contain genes for which there is no method of selection.

It is another object of the present invention to provide a method for preparing DNA fragments which contain a tumor suppressor gene.

It is another object of the present invention to provide cells which contain a heterologous DNA fragment which contains a gene for which there is no method of selection.

It is another object of the present invention to provide cells which contain a heterologous DNA fragment which contains a tumor suppressor gene.

These and other objects, which will become apparent during the following detailed description, have been achieved by the inventors' discovery that, by irradiating a microcell, which contains a chromosome and into which a selectable marker gene has been introduced, with 1,000 to 100,000 rads of $\gamma$-irradiation, it is possible to obtain chromosomal fragments (DNA superfragments) having from 1 million to 100 million base pairs and that these DNA superfragments may be introduced into cells and screened for the expression of any particular gene product, to facilitate the rapid cloning of a gene even if no selection method for the gene exists.

Thus, the present objects have been achieved by: A method for forming a DNA superfragment, comprising:

(i) irradiating microcells, which contain a chromosome that contains a first and a second marker, with $\gamma$-irradiation of a dosage of 1,000 to 100,000 rads.

The method of cloning a gene, comprising:

(i) introducing a foreign chromosome, containing a first marker, into a host cell, wherein the genome of said host cell does not contain said first marker;

(ii) introducing a second marker randomly in said foreign chromosome to obtain chromosomes which correspond to said foreign chromosome and contain both said first and said second marker;

(iii) selecting for cells which contain chromosomes having said second marker to obtain a first cell culture which contains cells that contain chromosomes having said second marker, and which does not contain cells that do not contain chromosomes having said second marker;

(iv) forming first microcells from cells of said first cell culture;

(v) fusing said first microcells to recipient cells, to obtain fused cells;

(vi) culturing said fused cells to select for the presence of chromosomes which contain both said first marker and said second marker, to obtain a second cell culture, which contains cells that have a chromosome containing both said first and said second marker, and which does not contain cells that do not have a chromosome containing both said first and said second marker;

(vii) forming second microcells from said second cell culture;

(viii) irradiating said second microcells, with $\gamma$-irradiation, to obtain irradiated microcells;

(ix) fusing said irradiated microcells with second recipient cells, to obtain second fused cells; and (x) culturing said second fused cells to select for the presence of a DNA fragment which contains said second marker, to obtain a third cell culture which contain cells that have a DNA fragment containing said second marker and which does not contain cells that do not have a DNA fragment containing said second marker.

A fragment of chromosomal DNA which contains from 1 million to 100 million base pairs.

A fragment of chromosomal DNA having from 1 million to 100 million base pairs, prepared by a process, comprising:

(i) irradiating a microcell with sufficient $\gamma$-irradiation to produce said fragment.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 4 (parts a–d) illustrates the morphology of tumor cells whose growth is abrogated by specific DNA superfragments.

DETAILED DESCRIPTION OF THE PREFERRED EMBODIMENTS

Figure 1:
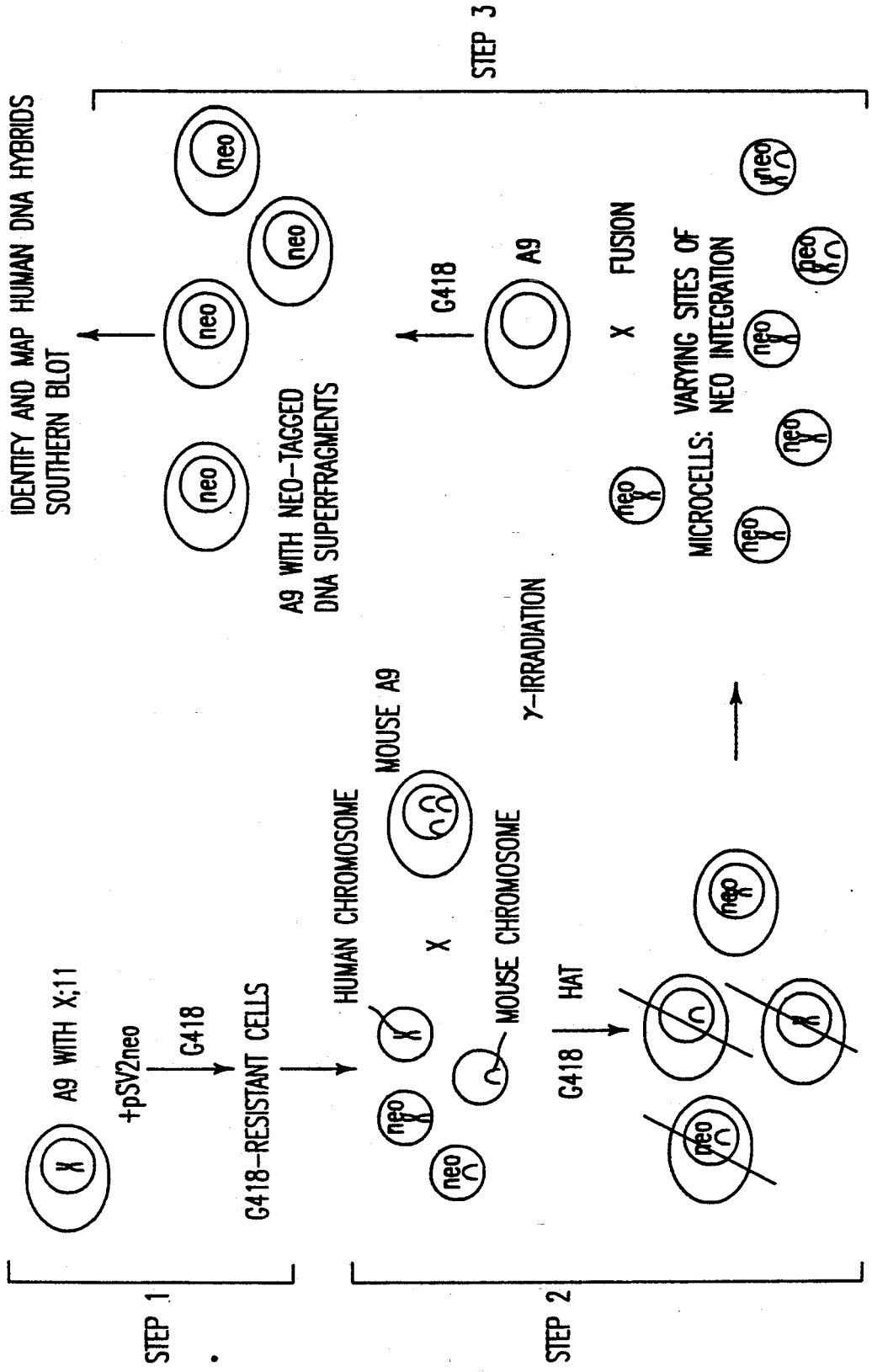
FIG. 1 illustrates schematically a preferred embodiment of the present method.

Thus, one aspect of the present invention relates to a method for isolating (cloning) from the human or other genome any gene for which one can screen but for which one cannot select. Screening means that the gene has not yet been cloned, but an assay for the gene's properties exists. Most genes satisfy this condition, because it is the normal or abnormal function of a gene that generates interest in it. In contrast, there are only a few genes for which one can select. Selection requires the existence of a chemical or physical method for destroying all cells that do not contain the gene of interest or for isolating the cell from cells that do not contain the gene. This is rarely true in modern genetic technology, since most of the genes for which biochemical selection is possible, generally those involved in metabolism, have already been isolated in the previous two decades.

Examples of genes for which the present method is useful include the most important genes in cancer genetics, namely those that suppress the development of malignancy, which can be screened for but cannot be selected for. Thus, tumor suppressor genes, when placed into cancer cells, cause the tumor cells either to become non-tumorigenic or to lose their capacity for unlimited self-renewal, i.e., senesce (a screening test). However, they cannot be selected for since cancer by its very nature selects against those cells that contain a suppressor gene. It is believed that inherited tumor suppressor genes underlie a large number of cancers in the general population. Thus isolation of these genes would allow one to detect people at risk of developing malignancy and perhaps prevent a large number of cancers that would otherwise develop (Li, F. P., "Familial Cancer Syndromes and Clusters", *Current Problems in Cancer*, vol. 14, pp. 73–114 (1990)). Furthermore, suppressor genes may lead to gene therapy for cancer.

As described in detail below, the present method has been used to isolate one of these tumor suppressor genes. Thus, a "DNA superfragment" that causes a variety of tumor cells to die when it is introduced into them, has been isolated. The present method may also be suitably applied to the cloning of many other disorders of man which can also be screened for but cannot be selected for. Furthermore, the present method may be suitably used to clone many genes in human and other mammalian cells that are of great interest but are not necessarily associated with a disease state, such as integral membrane proteins, genes that affect intercellular communication, genes that control the function of the nervous system, genes that cause cellular aging, and large genes that cannot be isolated by conventional means.

Current technology allows one to transfer an entire genome into a recipient cell (cell fusion), or to transfer a specific chromosome into a recipient cell (monochromosome transfer). These assays allow one to show that a gene is present in one cell and not another, or that a gene is on a particular chromosome. However, the average human chromosome contains one hundred thirty million base pairs of DNA (range approximately 50 to 240 million base pairs), or one hundred thirty times (range 50 to 240 times) the amount of DNA present in a bacterial cell. Thus, it has been impractical to isolate a gene from an entire human chromosome directly. On the other end of the scale, one can transfer individual genes into recipient cells. Of course, one does not have the gene in hand when one begins one's search for a gene. At a slightly more sophisticated level, one can transfer approximately 250,000 base pairs of human genetic material in the form of a yeast artificial chromosome (YAC). Again, however, it is impossible to generate yeast artificial chromosomes from an entire chromosome (which would require thousands of YACs), map each YAC back to the region of interest, and then test each YAC individually in a screening test for the property that the gene confers.

However, by fragmenting a human chromosome into ten to 200 pieces, of 1 million to 50 million base pairs, according to the present invention, which can be individually transferred into any recipient mammalian cell, it becomes practical to determine which of these fragments contains the gene of interest. It is then considerably easier to isolate the gene of interest from this "DNA superfragment". The average DNA superfragment of the present invention contains two to five million base pairs of DNA, and these fragments can be transferred to recipient cells to screen for the presence of the gene. The conventional cloning strategies, that the present method replaces, must begin with at least one hundred times as much DNA (i.e., a chromosome), if one wishes to screen for the presence of the gene using the currently available art. Thus, the complexity and time required for cloning a gene is reduced by the present method by at least one hundredfold. Thus, the effort required for cloning a gene of interest is reduced to only the time required to perform the screening test for the gene, which would vary from days to weeks depending upon the laboratory project, but in any case would be the standard assay technique for that laboratory. Furthermore, use of the present superfragments requires no special skill and allows generation of a very small number of candidate clones containing the gene.

Thus, the present invention provides a generalized method for isolating fragments of chromosomes that contain a mammalian selectable marker, allowing one to introduce any desired DNA superfragment into virtually any cell. While some hybrid panels already exist for selected chromosome fragments (T. Glaser et al, "A Fine Structure Deletion Map of Human Chromosome 11p: Analysis of J1 Series Hybrids", *Somatic Cell Mol. Genetics*, vol. 15(6), pp. 477–501 (1989)), they cannot be transferred into recipient cells for screening purposes. The present DNA superfragments can be transferred into virtually any recipient cell. In addition, fragments in existing hybrids (which lack the ability to be transferred) also generally contain too much DNA for cloning to be practical. The present method allows one to generate arbitrarily small fragments, eliminating the need to study DNA outside the immediate vicinity of the target gene. Again, this requires that one be able to transfer the fragment into recipient cells to screen for the gene, an advantage of the present method. Furthermore, the present method enables one to transfer the gene of interest in its appropriate chromosomal context, ensuring normal regulation of the gene.

As noted above, while very large genetic units (whole genome or chromosome) can be transferred, as can very small genetic units (bacteriophage or YAC), there is no way at present to transfer intermediate-sized functioning genetic units (such as the present DNA superfragments). For convenience, the size of each of these units is shown below:

| Sizes of Complementing Genetic Units (Example: Human) | |
|---|---|
| Transferrable unit | Average size (bp) |
| Genome | 3,000,000,000 |
| Chromosome | 130,000,000 (average) |
| DNA superfragment | 1,000,000 to 100,000,000 |
| YAC | 250,000 (average) |
| Bacteriophage | 15,000 (average) |

Accordingly, the present method makes it as easy to study the human genome as it has been to study the bacterial genome, which is one thousand-fold less complex. For example, with two people working for one year (including methodological development), it has been possible to isolate approximately 100 DNA superfragments comprising all of chromosome 11, each of which can be transferred to recipient cells independently. Thus, the entire human genome may be fractionated and isolated in a similar manner in two years by a staff of about twenty. With the present method, it is possible to clone genes directly from the "top down," isolating from a chromosome the DNA superfragment containing the gene. Using already available techniques, it is then relatively straightforward to isolate the gene from this superfragment. Thus, the present method renders conventional chromosomal walking completely unnecessary.

The present method will now be further described in the context of a specific example. However, it is to be understood that the present invention is not limited to the specific example.

Currently available technology allows one to isolate a single chromosome in a rodent background. In the test case of chromosome 11, a previously isolated monochromosome hybrid that contained a human translocation chromosome, with most of chromosome 11 and a small portion of the X chromosome (L. Bonetta et al, "Wilms Tumor Locus on 11p13 Defined by Multiple CpG Island-Associate Transcripts", *Science*, vol. 250, pp. 994–997 (1990) and M. Koi et al, "Construction of Mouse A9 Clones Containing a Single Human Chromosome (X/Autosome Translocation) via Micro-cell fusion, *Jpn. J. Cancer Res.*, vol. 80, pp. 122–125 (1989)) was chosen as the starting point. The portion of the X chromosome contains the HPRT gene which allows selection in "HAT" media (Littlefield, J.W., "Selection of hybrids from matings of fibroblasts in vitro and their presumed recombinants", *Science*, vol. 145, pp. 709–710 (1964)). Thus, the starting point cells were mouse cells containing essentially all of human chromosome 11 as the only human material. Preparation of these single whole chromosome hybrids may be accomplished by conventional techniques.

The breaking of the human chromosomes into DNA superfragments, that can be transferred to mammalian cells, involves three essential steps. First, a neomycin resistance gene, pSV2neo, was introduced by transfection into the microcell hybrid containing human chromosome 11. This gene integrates randomly into both the human chromosome (number 11 in this instance) and the many mouse chromosomes in the hybrid cell. The objective at this step is to generate hundreds or thousands of colonies containing neo at many different sites of integration into chromosome 11.

The second step is the selective transfer into mouse cells of many human chromosome 11's each carrying the pSV2neo gene at varying locations along the chromosome. For this step, 200 to 1,000 G418-resistant colonies from the first step are pooled (neomycin confers resistance of mammalian cells to the antibiotic G418). "Microcells", generally containing one chromosome each, are prepared from the whole cells within these pools. The microcells are then fused to mouse cells using polyethylene glycol, and selection for surviving cells with both G418 and HAT is performed. Four types of cells can result. First, recipient cells might contain only a transferred mouse chromosome with neo, but these will die in the presence of HAT. Second, cells containing a transferred mouse chromosome without neo will also die. Third, recipient cells might contain the human chromosome without neo. These will also die in the presence of G418. Finally, recipient cells may contain the human chromosome with neo, and only these cells will survive.

In the unlikely event that a microcell contains two chromosomes, one being a mouse chromosome containing neo and the other being the human chromosome, despite the statistical unlikelihood and the fact that the microcells are filtered in order to select for those containing only one chromosome, this eventuality will be apparent in the final characterization by Southern blotting as there will be no human DNA in that fragment.

The third step is the fragmentation of these neo-tagged human chromosomes by γ-irradiation. Microcells (generally containing one chromosome) are again prepared from whole cells, but this time from the HAT/G418-resistant colony pools. Prior to microcell fusion, the microcells themselves are subjected to γ-irradiation. This irradiation fragments the chromosomes and separates the neo-containing "DNA superfragment" from the other fragments that are generated. This is an important and non-obvious step, since if one irradiates whole cells and then performs microcell (chromosome) transfer, the dose of irradiation must be quite small or else the donor whole cells will not be viable and microcell transfer will be unsuccessful. Thus, it is possible to use doses of 10,000 rads or more, as compared to the usual 300 rads used in whole cell irradiation, and thus generate much smaller fragments than is otherwise possible. In experiments by other laboratories in which irradiation is used on whole cells prior to chromosome transfer, deletion hybrids are generated where most of the chromosome is transferred but a small portion is missing. By using a very high dose of radiation on the microcells, according to the present method, most of the chromosome is missing, and only a small portion is retained. This is an important and fundamental difference, because one cannot clone a hole (deletion). That is, if one transfers most of a chromosome but with a small portion missing, where the missing portion contains the gene, one cannot use that hybrid in order to clone the gene. On the other hand, by the present method, only a small portion of the chromosome is transferred, and one can easily clone the gene from such a small fragment. However, it is not possible to achieve this result unless one irradiates the microcells rather than the whole cells prior to fusion.

An alternative technique of irradiating whole cells at a high dose of radiation followed by whole cell fusion, rather than microcell transfer, also could not be used to screen for genes by their phenotypic expression, because species in which the resulting heterokaryons can survive (e.g., hamster) serve as poor microcell donors for subsequent transfer to the recipient cells to be screened. The resultant hybrids would contain as many as one hundred chromosomes. Unless one can transfer the fragment into any recipient cell, one cannot screen for the properties of the gene. Irradiation of the microcells themselves rather than the intact donor cells is not a standard technique, has not been reported, and normally would not be desired in ordinary mapping experiments where the resultant hybrid would not be subjected to further transfer and screening of recipient cells. This is because one would be concerned about the risk of fragmentation or rearrangement of the chromosomes if one irradiates them directly. Thus, irradiation of the microcells rather than the donor cells might lead to recipient cells less suitable for mapping than irradiation of the donor cells. However, rearrangements within the microcells, if they exist, do not cause a problem in the present method of cloning, since the issue here is the ability to transfer a functional gene into any recipient mammalian cell, not the specific order of the genes within the hybrid. Breakage or rearrangement could become a problem if it occurred over the region normally spanned by a gene. However, the inventors have determined that regions of up to one million base pairs remain intact by the present method, and that genes do retain their functional properties when transferred by the present method.

Figure 2:
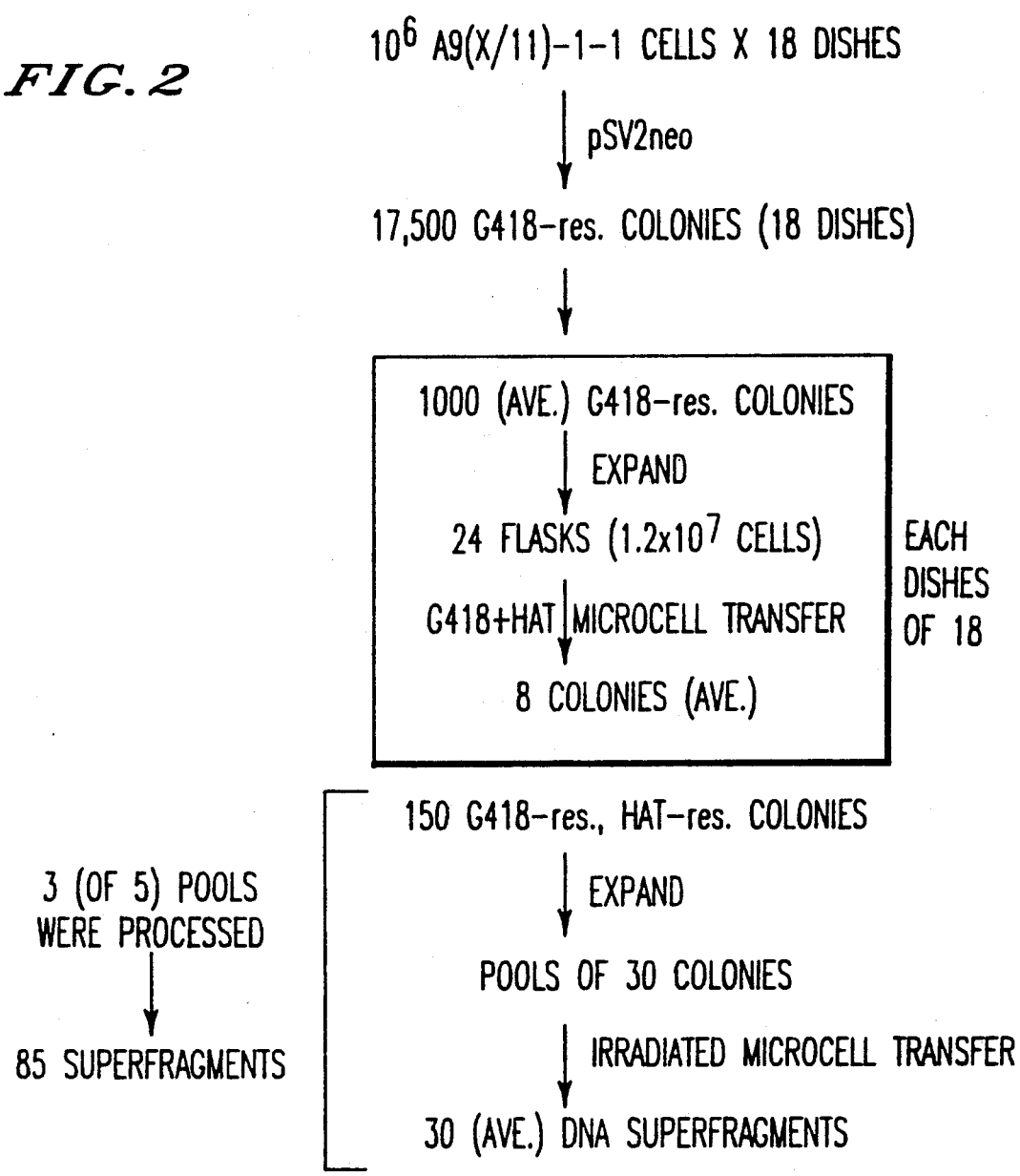
FIG. 2 also illustrates a preferred embodiment of the present invention.

In addition, while microcell transfer has been done before, and neo transfection has been done before, neo transfection followed by microcell transfer to generate a large number of hybrid cells containing neo randomly integrated throughout a given human chromosome is previously unknown. On the face of it, the expectation of success of such an effort would appear low since the neo could go into the many mouse chromosomes also present within the cell. However, starting with 17,500 G418 resistant colonies and by selection for both neo integration and chromosome 11 in the second step, described above, approximately 150 distinct monochromosome hybrids with varying sites of neo integration could be generated. In the present Example, 90 of the 150 G418 and HAT resistant colonies were processed through the irradiation microcell step resulting in the isolation of 85 superfragment clones, supporting the above estimate. (See FIG. 2). The experimental data on chromosome 11 described below support this estimate. Thus, it is the combination of marker (such as, e.g., neo) integration, chromosomal fragmentation, and effective transfer to recipient cells that has resulted in the success of the present cloning method.

A schematic summary of a preferred embodiment of the present method is shown in FIG. 1. In step 1, A9 mouse cells which contain a translocation X;11 (most of chromosome 11 with a small portion of the X chromosome containing the HPRT gene, selectable in HAT medium) are transfected with pSV2neo to incorporate neo (which confers G418 resistance) randomly throughout the mouse and human DNA. Step 2 involves selecting for both G418 and HAT resistance, to obtain those cells in which neo has been incorporated into the human chromosome. In step 3, microcells obtained from the G418 and HAT resistant colonies are exposed to γ-irradiation to obtain microcells containing DNA superfragments. Since the neo gene was incorporated randomly throughout the human chromosomes, superfragments corresponding to different regions of the human chromosome and also containing neo will be formed. The irradiated microcells are then fused with mouse A9 cells and selected on the basis of G418 resistance. The high molecular weight genomic DNA is isolated from the G418 resistant colonies, and the presence or absence of individual genes or DNA fragments is ascertained by Southern blotting.

The DNA superfragments may then be transferred into recipient cells of choice, which can then be screened for the presence or absence of a property conferred by a particular gene product. Since the present isolated superfragments all contain a marker, such as, e.g., neo, it is possible to conduct an initial selection for the recipient cells which contain a superfragment (e.g., selection based on G418 resistance).

The individual superfragments may then be screened for a particular gene as follows. A single superfragment is introduced into a screening cell, which is known not to possess the gene in question, e.g., the tumor suppressor gene. The introduction of the superfragment into the screening cell may be carried out by conventional microcell transfer (R. E. Fournier et al, "Stable association of the human transgenome and host murine chromosomes demonstrated with trispecific microcell hybrids", *Proc. Natl. Acad. Sci USA*, vol. 74(9), pp. 3937–3941 (1977)). In this way, it is possible to produce a series of strains of screening cells which differ only in regard to which superfragment they contain. The various strains are then screened for the presence of the property of the specific gene product. In the case of a tumor suppressor gene and a tumor cell screening cell, the presence of the gene may be screened for by determining which superfragment(s) result in an abrogation of tumor cell colony growth in vitro or in vivo.

Figure 3:
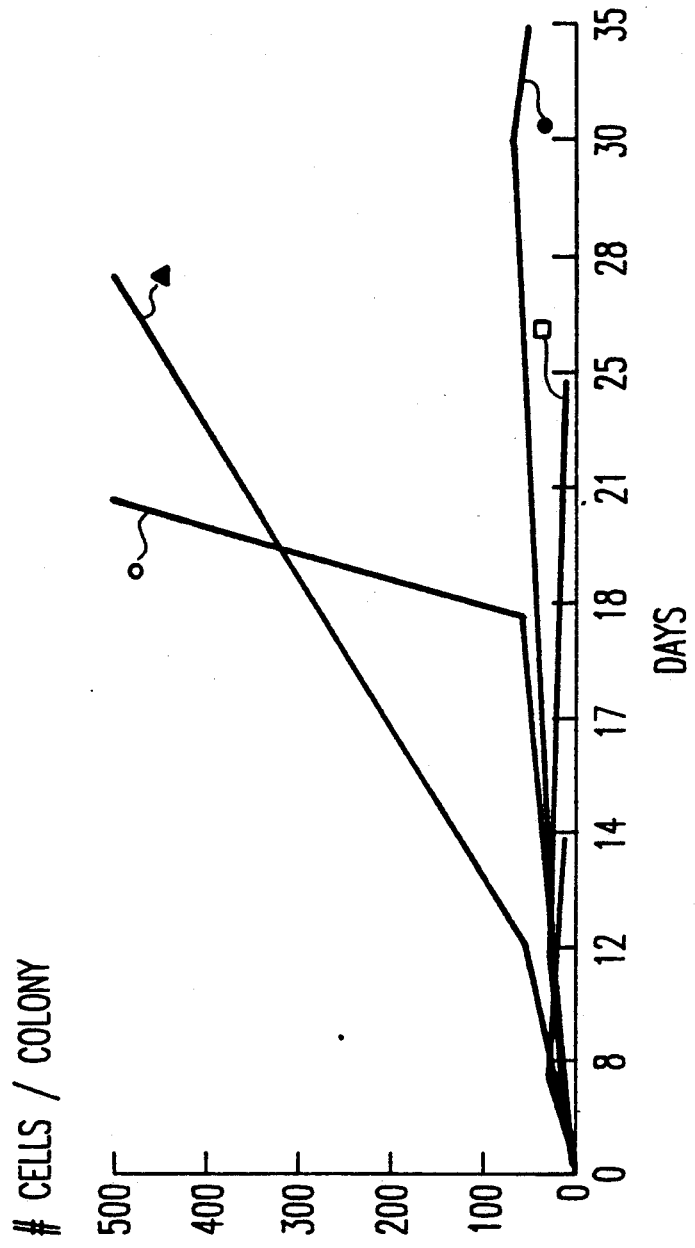
FIG. 3 illustrates the growth rate of colonies of tumor cells containing various DNA superfragments (Δ, 11sup/51-6; ○ 11sup/21-5;; □ 11sup/74-1; ▲, 11sup/11-2; and ●, 11sup/52-1).
Figure 4A:
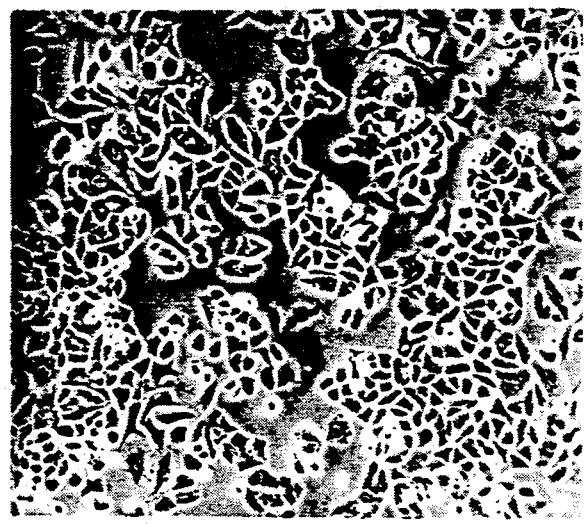
FIG. 4a: Wilms tumor cells having received a nonsuppressing superfragment.
Figure 4B:
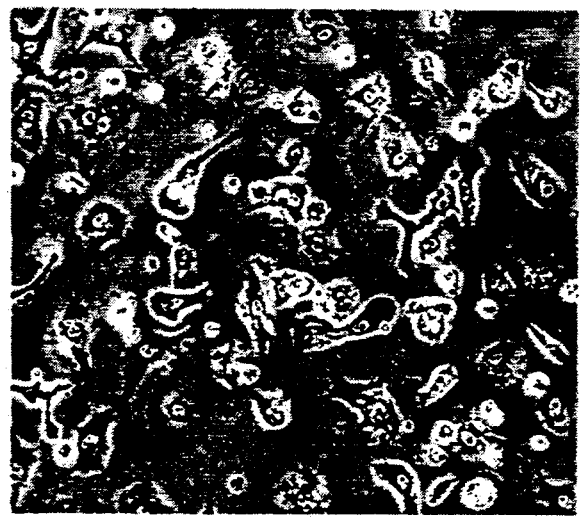
FIG. 4b: Wilms tumor cells having received a suppressing superfragment.
Figure 4C:
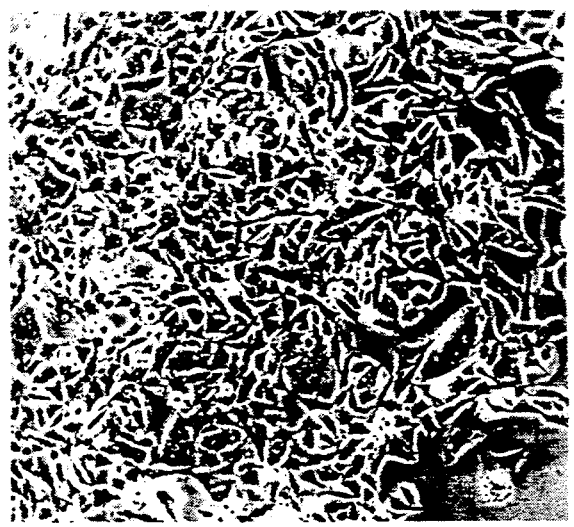
FIG. 4c: control rhabdomyosarcoma cells.
Figure 4D:
FIG. 4d: rhabdomyosarcoma cells suppressed by a DNA superfragment.

FIG. 3 shows the results of just such a screening method. Thus, curves Δ, □, and ● show an abrogation of tumor cell colony growth, indicating that the superfragments introduced into these cells contain the tumor suppressor gene. In contrast, curves ○ and ▲ do not show any abrogation of colony growth, indicating that the tumor suppressor gene is not present on the superfragments introduced into these cells.

FIG. 4 depicts the morphology of tumor cells which have had a superfragment introduced therein. FIGS. 4b and 4d are exemplary of the morphology of cells in which a superfragment containing the tumor suppressor gene has been introduced, while FIGS. 4a and 4c represent examples of cells which do not contain a superfragment containing the tumor suppressor gene.

Of course, the present method is not limited the abovedescribed example. Rather, the present method can be applied to any chromosome of any species for which one can generate microcells, such as mammalian systems (including humans), birds, fish, and amphibians. The present method may also be applied to plant chromosomes by the use of protoplasts and yeast by protoplast fusion (M. Ward et al, "Transfer of antibiotic resistance genes between yeast and mammalian cells under conditions favoring cell fusion", *Somatic Cell, Mol. Genet.*, vol. 12, pp. 101–109 (1986)).

In addition, a variety of schemes for first generating the individual monochromosome that will be fragmented may be employed. For example, the whole chromosome may be first selected for by biochemical means (available for all human chromosomes except 6, 11, 15, and Y) or by using other chromosomal translocations (all human chromosomes are encompassed by one of these two methods), or even with another antibiotic resistance gene transfected into the recipient chromosome under conditions that provide a single locus of integration. Furthermore, different antibiotic selection genes such as hygromycin or mycophenolic acid may be utilized. In addition, auxotrophic markers, such as his, lys, etc. may be used. In other words, the first marker may be any selectable marker which can be introduced into or occurs naturally on the chromosome of interest but is not present in the genome of the initial host cell.

Likewise, the second marker is not limited to neo, but can be any selectable marker that can be introduced randomly throughout the chromosome of interest. Other suitable examples include those markers discussed above which can be incorporated into the chromosome. In addition, neo need not be introduced by way of pSV2neo. Alternatively, neo may be introduced by way of pcDneo.

Furthermore, the host and first recipient cells need not be mouse A9 cells, but can by any cells in which the chromosome of interest and DNA superfragments are replicated. Suitable examples include other mammalian cells or cells of the same species of the chromosome of interest. For convenience, it is preferred that the host and first recipient cells be the same, and mouse A9 cells are preferred.

The dose of radiation of the microcells may also be varied. The dose may be raised to arbitrarily high levels to generate much smaller DNA superfragments. Although DNA superfragments may be generated under both low and high radiation conditions, the dose of $\gamma$-irradiation is suitably 1,000 to 100,000 rads, preferably 5,000 to 50,000 rads, more preferably 10,000 to 20,000 rads, most preferably about 10,000 rads, resulting in superfragments having 1 million to 100 million base pairs, preferably about 1 million to 5 million base pairs. The investigator may then utilize large DNA superfragments of two to five million base pairs, screen for those containing the gene of interest, and then utilize smaller superfragments of 300,000–1,000,000 base pairs, further reducing the overall effort.

In the present Example, the source of $\gamma$-irradiation was a cesium irradiator. However, other suitable sources may be used.

The advantages of the present invention are as follows. First, without prior knowledge of a specific chromosomal location but only general knowledge of the chromosome containing the gene, it is possible to determine which DNA superfragment contains the gene of interest. In doing so, a fragment containing only that gene and the surrounding DNA will have been isolated. Looked at another way: rather than cloning a gene using a conventional genomic library, containing the equivalent of $3 \times 10^9$ base pairs of DNA, one can now abbreviate that process by using a specific DNA superfragment of $1\text{-}3 \times 10^6$ base pairs. Thus, the complexity of the cloning effort will be reduced by two to three orders of magnitude.

Second, the location of the gene on the chromosome is often ambiguous because of conflicting experimental data. Thus, for example, conflicting chromosomal deletion data has hampered the isolation of the tumor suppressor locus on the short arm of chromosome 3 involved in small cell lung cancer and renal cell carcinoma. Similarly, conflicting data on chromosomal losses has clouded the identification of tumor suppressor loci on the short arm of chromosome 11, with variable map locations suggested variously by studies on breast cancer, pediatric tumors, and lung cancer (S.L. Naylor et al, *Nature*, vol. 329, pp. 451–454 (1987); B. Zbar et al, *Nature*, vol. 327, pp. 721–724 (1987); and A.E. Reeve et al, *Molec. Cell Biol.*, vol. 9, pp. 1799–1803 (1989)). Since the present method allows one not only to localize the gene, but also to transfer the DNA fragment into the appropriate recipient cells, it is now possible to localize the functional property of the gene, and to isolate the gene in a much smaller genetic unit than was previously possible.

Third, the present method allows one to exploit the screening test at each stage of molecular cloning. Currently, one has an assay at the chromosomal or whole cell level, but then loses it when one embarks upon chromosome walking strategies, since the intermediate products of chromosomal walking lack a functionally active gene. Another way of stating this is that in conventional approaches one does not know if one is walking in the right direction, and one does not know if one has walked too far. Our process obviates both of these limitations.

Other features of the invention will become apparent in the course of the following descriptions of exemplary embodiments which are given for illustration of the invention and are not intended to be limiting thereof.

EXAMPLES

Method for Constructing DNA Superfragments

I. Construction of Mouse A9 Cells Containing a Single Human Chromosome

As a preliminary step, the human chromosome of interest was isolated in a rodent background. In this case, chromosome 11, a human fibroblast translocation cell line containing most of chromosome 11, with a small portion of the X chromosome useful for biologic selection (i.e., containing the HPRT gene, selectable in HAT medium, J.W. Littlefield, *Science*, vol. 145, pp. 709–710 (1964) was the starting point. However, the same approach may be used for any human chromosome by exploiting either (a) natural selectability of the chromosome in auxotrophic medium, which can be used for all chromosomes except 11, 15, and Y (D. Patterson, *Medical Genetics:*1987, pp. 144–155, Fnd. for Adv. Education in the Sciences, Inc. (1987)); (b) integration of a different selectable marker (e.g., a gene for hygromycin resistance); or (c) other X-autosome translocation cell lines. Furthermore, the same rationale applies to other chromosome donor species, such as mouse and Drosophila. These would include, but are not limited to a gene on chromosome 4 that causes HeLa cells to senesce (it is difficult to clone the gene because the recipient cells cannot be grown); and chromosomes that contain genes encoding iontophore channels; opiate and other drug receptors; gap junction proteins; genes involved in electrical excitation; genes that cause cellular aging; or any gene with >30 kb or having cDNA which exceeds 5 kb.

The human chromosome is best first isolated in mouse cells by cell fusion followed by microcell transfer. If one wants to transfer the DNA superfragments eventually into mammalian cells, then the best eventual donor cell for the DNA superfragments is mouse A9 cells. Given this fact, mouse A9 cells must be the recipients of the irradiated chromosomal material. We have found experimentally that the best cell line for the donor chromosome to the mouse cells is also mouse A9 cells. The essential problem, then, is transferring a small portion of the human chromosome from one mouse A9 cell to another mouse A9 cell. If one irradiates at a low enough level (e.g., 300 rads) to allow microcell transfer (at higher radiation level, the cell is not viable enough for microcell transfer), then the DNA fragments that are transferred are too large (i.e., representing most of the chromosome). If one irradiates whole cells at a high radiation level (e.g., 10,000 rads), then one cannot perform microcell transfer, but only a simple cell-to-cell fusion. However, the present results show that the resultant mouse cell will have too many chromosomes for subsequent microcell transfer. Thus, no cell hybrids were formed, after fusing intact A9 and $\gamma$-irradiated A9 cells, indicating that isolation of the chromosomal subfragment will be impossible. The present method, as described below, circumvents these problems and offers a generalized method for introducing a mammalian selectable marker gene (such as, e.g., neo) in each fragment that is isolated.

A. Isolation of Hybrid Cells Formed Between Mouse A9 Cells and Human Cells.
1. $10^6$ cells of each parental cell line are mixed and cultivated for 2 days.
2. Cells are fused by polyethylene glycol (PEG, MW 1000; 1 min, 5 ml of 41.5% PEG containing 15% dimethyl sulfoxide [DMSO]), followed by extensive washing with serum free Dulbeccol's Modified Eagle's Medium (DMEM).
3. After 2 days of cultivation in DMEM containing 10% fetal calf serum (FCS), the culture medium is replaced by selective medium (in the test case, containing hypoxanthine/aminopterin/thymidine [HAT] plus ouabain).
4. After 6 weeks of cultivation, hybrid clones are isolated, expanded and karyotyped. A clone which contains the expected human chromosome is chosen as microcell donor.

B. Microcell Transfer of Human Chromosome from the Hybrid Cells to Mouse A9 Cells.
1. Hybrid cells ($10^6$) are inoculated into 25 cm$^2$ flasks and incubated for one or two days. Micronuclei are induced by colcemid (0.05 $\mu$g/m) for 48 hours in DMEM containing 20% FCS and selective medium (in the test case, HAT).
2. Flasks are filled to the neck with serum-free DMEM containing 10 $\mu$g/ml of cytochalasin B. Enucleation is performed by centrifugation, at 8300$\times$g for 1 hour, of entire flasks placed in a rotor filled with tempered water. In order to prevent breakage of the flasks, the flasks are wrapped with 2.5 cm wide paper tape 4 to 5 times around the shoulder. The rotor used is a Sorvall GSA (DuPont Instruments).
3. Microcells at the bottom of the flasks are collected in serum-free medium and the cell suspension is filtered through 8 $\mu$m, 5$\mu$m and 3$\mu$m polycarbonate filters in series.
4. The purified microcells are pelleted by centrifugation at 400$\times$g for 7 minutes and resuspended in 2 ml of serum-free medium containing phytohemagglutinin (PHA, 100 $\mu$g/ml).
5. The microcells are attached to prewashed A9 cell monolayers (1–2$\times 10^6$ cells) by incubation for 15 min at 37° C.
6. The cells are fused by treatment with 3 ml of 47% PEG (M.W. 1540) solution for 1 min, followed by extensive washing in serum-free medium. After 1 day of incubation in growth medium, cells are trypsinized and plated over 10 plates (100 mm) containing selective medium (in this case, HAT). Microcell hybrids are isolated following cultivation for two weeks.
7. The resulting microcell hybrids are cloned, expanded and karyotyped. A clone which contains the desired human chromosome as the sole human chromosome in a mouse background is chosen for further experiments.

II. Isolation of G418-resistant Human Monochromosomal Mouse A9 Hybrids

A. The cells which contain a single human X;11 chromosome ($10^6$ cells) are seeded in a 100 mm dish. The cells are grown in selective medium (in this case, DMEM containing 10% FCS and HAT), supplemented with 10% FCS, for one day.
B. pSV2neo plasmid DNA was prepared by lysozyme-alkali procedure followed by two cycles of CsCl equilibrium density gradient centrifugation and repeated phenol extractions. Plasmid DNA (10~30 $\mu$g) is mixed with 0.5 ml of 0.25 M CaCl$_2$. 0.5 ml of 2$\times$BES-buffered saline (2$\times$BBS) containing 50 mM N,N-bis-(2-hydroxyethyl)-2-aminoethanesulfonic acid (pH 6.95), 280 mM NaCl and 1.5 mM Na$_2$HPO$_4$ is added, and the mixture is incubated for 20 min at room temperature.
C. Calcium phosphate-DNA solution (1 ml) is added to the culture of cells, and the culture is incubated for 18 h at 35° C. under 3% CO$_2$.
D. The medium is removed, and the cells are washed with growth medium, refed, and incubated for 24 h at 37° C. under 5% CO$_2$.
E. The cells are incubated for an additional 24 h before selection with G418 (400 $\mu$g/ml).
F. The cultures are cultivated for 2–3 weeks. G418-resistant colonies are formed at a frequency of about 1$\times 10^{-3}$ treated cells. In this case, 17,500 G418-resistant cells were obtained from about 1.8$\times 10^7$ pSV2neo-treated cells in 18 dishes.

III. Selective Transfer to Mouse A9 Cells of the Selected Human Chromosome Tagged with the pSV2neo Gene A. An average of 1,000 G418-resistant colonies are pooled and incubated in G418-containing medium until they reach confluence in a 75 cm$^2$ flask or 150 mm dish.
B. Microcell transfer of the neo-tagged human chromosome X/11 to A9 cells is performed by the method described in section IB above. 24 flasks (containing 1.2$\times 10^7$ cells) are used in each microcell transfer experiment. An average of 8 colonies are obtained after selection of the fused culture against HAT+G418. These experiments are performed 18 times resulting in a total of approximately 150 HAT+G418 resistant colonies.

C. The resulting clones are individually isolated and cryopreserved at −135° C., in DMEM, 10% FCS, 10% DMSO.

Fragmentation of Neo-tagged Human Chromosomes by γ-Irradiation

A. Of the 150 HAT+G418 resistant colonies prepared in IIIB, approximately 30 are thawed, grown individually to $5 \times 10^5$ cells, pooled, and incubated further until they reach confluence in 150 mm dishes. Microcells are prepared from about $10^7$ colcemid treated cells in 12 flasks (25 cm$^2$) and pelleted in 15 ml conical tubes. The cells are resuspended in 0.5 ml of serum-free medium and subjected to γ-irradiation. Three independent pools of 30 were processed as above (90 of the 150).

B. The microcells are irradiated in a cesium irradiator with 10 krad of γ-rays at room temperature. 2 ml of 100 μg/ml PHA are added to the cell suspension and the microcells are attached to an A9 cell monolayer by incubation for 15 min at 37° C. Note that the microcells themselves are subjected to γ-irradiation. This irradiation fragments the chromosomes and separates the neo-containing "DNA superfragment" from the other fragments that are generated. This is an important distinction, since if one irradiates whole cells and then performs microcell (chromosome) transfer, the dose of radiation must be quite small, or else the donor whole cells will not be viable and microcell transfer will be unsuccessful.

C. The fused cultures are trypsinized after 24 h incubation, and the cells are replated to 10 plates (100 mm) containing DMEM 10% FCS with G418.

D. After 2-3 weeks in G418-containing medium, the resulting clones are isolated independently, expanded, and cryopreserved. In the test case, from 3 γ-irradiation experiments, 85 DNA superfragment clones were established from a single human chromosome.

E. High molecular weight genomic DNA is isolated from γ-irradiated, G418-resistant DNA superfragment clones. The presence or absence of individual genes or DNA fragments is ascertained by Southern blotting.

F. DNA superfragments generated at the radiation dose in the test case (10,000 rad) are approximately 1 to 5 megabases ($1-5 \times 10^6$ bp) in size. The size of the superfragments can be reduced or increased by using higher or lower doses of radiation, respectively.

G. The human chromosome-specific DNA superfragments are subjected to a second microcell transfer in order to further purify the neo-tagged superfragment. The purpose of this second transfer is that occasionally a non-neo-containing fragment is also present after the first transfer, but the neo-containing DNA superfragment is then easily purified.

V. Transfer of DNA Superfragments to Recipient Cells

A. Transfer of DNA Superfragments
  1. For each DNA superfragment that is to be tested, hybrid cells ($10^6$) are inoculated into twelve 25 cm$^2$ flasks and incubated for 1-2 days. Micronuclei are induced by colcemid (0.05 μg/ml) for 48 h in growth medium containing 20% FCS, containing a reduced concentration of G418 (100 μg/ml).
  2. Flasks are filled up to the neck of the flask with serum-free DMEM containing 10 μg/ml of cytochalasin B. Enucleation is performed by centrifugation at 8300×g for 1 hour of entire flasks placed in a rotor filled with tempered water. In order to prevent breakage of the flasks, the flasks are wrapped with 2.5 cm wide paper tape 4~5 times around the shoulder. The rotor used is Sorvall GSA (DuPont Instrument).
  3. Microcells at the bottom of the flask are collected in 20 ml of serum-free medium and filtered serially through 8 μm, 5 μm, and 3 μm polycarbonate filters.
  4. The microcells are pelleted by centrifugation at 400×g for 7 min and resuspended in 2 ml of serum-free medium containing phytohemagglutinin (100 μg/ml).
  5. The microcells are attached to prewashed recipient cells of choice, such as Wilms tumor G401 or rhabdomyosarcoma (RD), that have been previously prepared as monolayers ($1-2 \times 10^6$ cells) by incubation for 15 min at 37° C.
  6. The preparation is treated with 3 ml of 47% PEG (M.W. 1540) for 1 min, followed by extensive washing in serum-free medium. After one day of incubation in growth medium, cells are trypsinized and plated in 4 plates (100 mm) containing G418. The concentration of G418 is cell line-dependent. Thus, recipient cells are previously tested at varying concentrations of G418 in order to determine the minimal cytotoxic dose. In the instance described here, a concentration of 400 μg/ml was used.
  7. The recipient test cells containing the DNA superfragments of interest are grown in media containing G418 for 14 days. By that time all of the control recipient cells not containing DNA superfragments die, and only recipient cells containing DNA superfragments survive.

B. Isolation of colonies of recipient cells containing individual DNA superfragments.
  1. Each plate is washed twice with Hanks buffered salt solution (HBSS). A cloning cylinder is placed over each colony and HBSS containing 0.25% trypsin is added for 5 min. The suspension is removed with a micropipette and transferred to growth medium containing 10% FCS and G418 at the appropriate concentration. Individual colonies are expanded for 2 weeks in G418, after which time G418 is no longer required.
  2. All of the experiments described in the above sections are performed in the absence of bactericidal antibiotics (except for G418 in the case of neo selection), or antimycotics. However, these agents can be used in the expansion of recipient cells containing individual DNA superfragments from this point onward. The colonies are divided into two fractions, one half being used for phenotypic assay and the other for isolation of high molecular weight genomic DNA. The DNA is used in southern blot (Church, G.M. and Gilbert, W., *Proc. Natl. Acad. Sci. USA*, vol. 81, pp. 1991-1995 (1984)) experiments to determine the presence or absence of individual genes in order to confirm that the DNA superfragments have been transferred to the recipient cells. DNA probes are label by random priming (Feinberg, A.P. and Vogelstein, B., *Anal. Biochem.*, vol. 132, pp. 6–13 (1983)).

By this method, 85 superfragment clones have been isolated to date. However, only approximately 90 of the 150 G418-resistant, HAT-resistant monochromosome hybrids have been processed through the third step (irradiated microcell transfer), so this number is expected to increase by about one half. Cells containing each DNA superfragment are grown in 100 mm dishes with DMEM containing 10% FCS plus 400 μg/ml G418 until they reach confluence. The cells are washed once with 10 ml Hank's balanced salt solution and washed with 10 ml 0.25% trypsin solution. Trypsinized cells are collected in a 15 ml tube with 10 ml DMEM containing 10% FCS plus 400 μg/ml G418 and pelletted by centrifugation at 300 g for 5 min. The supernatant is aspirated and the cell pellet is resuspended in 3 ml DMEM containing 10% FCS and 10% DMSO. 1 ml of the cell suspension ($10^6$ cells) is inoculated into a 2 ml freezing vial. Three vials per each superfragment are stored at $-135°$ C.

VI. Screening for the Phenotype of Recipient Cells Containing Individual DNA Superfragments The specific application of this example is the identification of tumor suppressor genes, i.e., genes that abrogate part or all of the malignant phenotype when introduced into malignant cells. Thus, the description below applies to that specific application. However, the same method may be used with regard to any phenotypic property for which one can screen, including but not limited to the following: chromosomal fragility; cell surface binding properties; cell-cell interactions; physiological properties; morphological changes; growth properties in vitro or in vivo; or elaboration of specific proteins or other biochemicals.

In this example, the purpose is to isolate a tumor suppressor gene from chromosome 11. It is known that at least one tumor suppressor gene is located on chromosome 11, since when the entire chromosome is transferred to tumor cells (i.e., Wilms tumor, a childhood kidney tumor; and rhabdomyosarcoma, a muscle tumor), the ability of these cells to form tumors in animals is abrogated. The data on the location of this tumor suppressor gene is conflicting, with evidence suggesting that it might reside on band 11p13 (which includes approximately 5–8 million nucleotides of DNA) or, alternatively, on band 11p15, which includes approximately 15–30 million nucleotides of DNA, or even on 11q (the long arm of chromosome 11 containing approximately 80 million nucleotides of DNA, based on its relative physical length). The objective, then, was to isolate many different DNA superfragments from chromosome 11, and introduce then individually into tumor cells to determine which of these fragments, if any, suppress the tumor properties of the recipient cells. If this is accomplished, then a relatively small portion of genetic material, suitable for direct cloning of the responsible gene, a task which cannot be accomplished using a whole chromosome as the starting material, will have been isolated.

The introduction of the fragment into the screening cell is similar to the introduction into the recipient cell under part V. G418 resistance is used to insure that every member of a given colony has received the superfragment.

Figure 5:
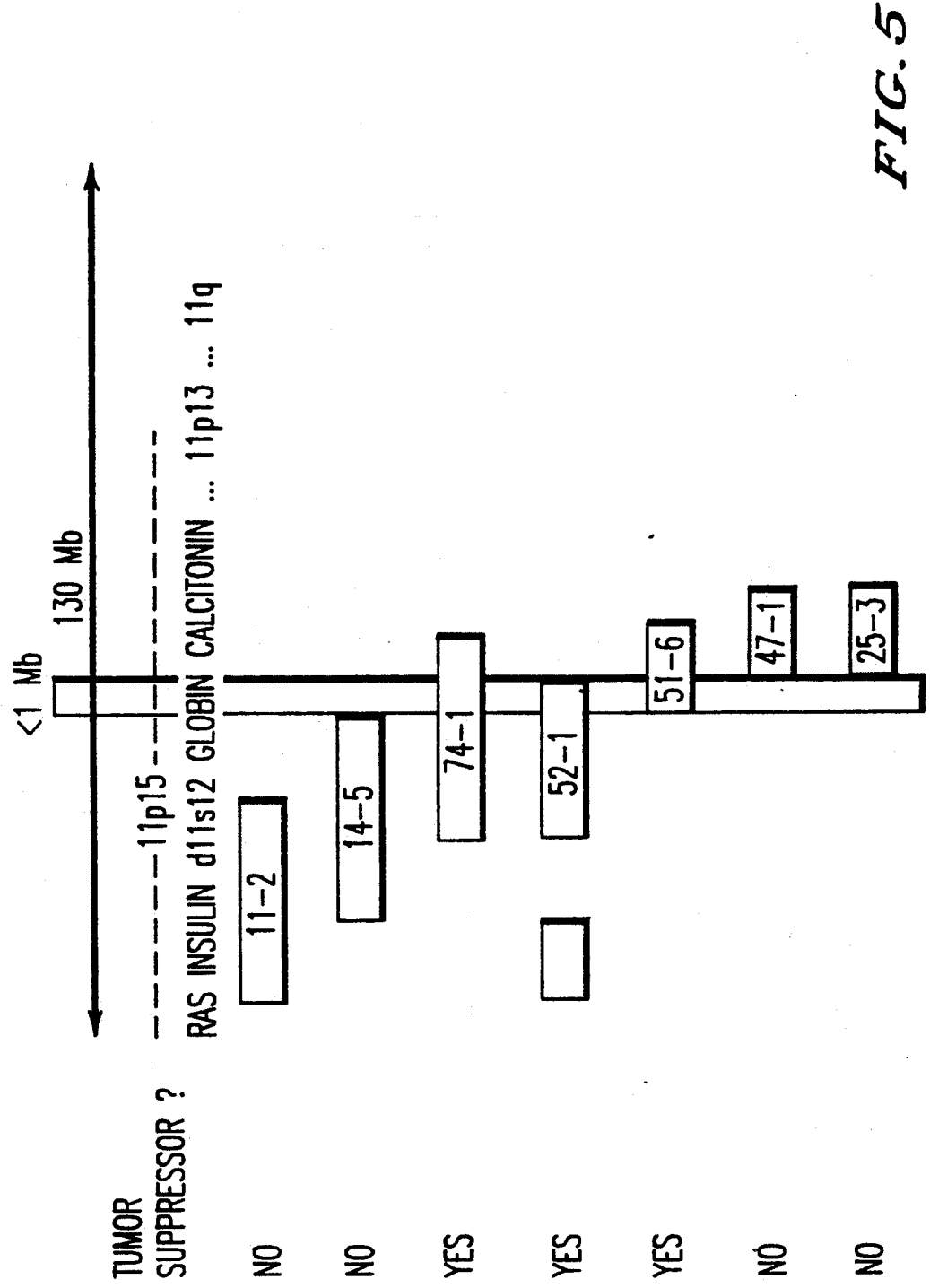
FIG. 5 illustrates graphically the DN that is present in the DNA superfragments that either do or do not abrogate the malignant phenotype.

The screening procedure for these cells is described below:

1. Individual colonies containing DNA superfragments were monitored for morphology and colony size. Each of the cells which had received a DNA superfragment was counted at each feeding, and photographs ware taken serially of these recipient cells.
2. Control tumor cells not containing DNA superfragments were observed in a similar manner.
3. As shown in FIG. 3, the growth of colonies of tumor cells (rhabdomyosarcoma) containing some DNA superfragments was substantially less than that of control tumor cells or colonies containing other DNA superfragments. Indeed, colonies that were suppressed by DNA superfragments ceased growing altogether. Thus, the growth of these tumor cells was abrogated by DNA superfragments 11sup/74-1, 11sup/52-1, and 11sup/51-6, when compared to DNA superfragments 11sup/11-2, 11sup/14-5, 11 sup/47-1, 11sup/25-3, and control cells. This phenotype represents cellular senescence. In essence, the cells have been "cured" of their malignant phenotype by the introduction of specific DNA superfragments, and these formerly malignant cells now die.
4. The morphology of recipient cells whose growth is abrogated by specific DNA superfragments also reverts to a nonmalignant appearance. As shown in FIG. 4, Wilms tumor cells receiving a suppressing DNA superfragment (11sup/52-1) (FIG. 4*b*) become flat in morphology, detach from the growth plate, and appear to die. For comparison, control Wilms tumor cells that have received a nonsuppressing superfragment (11sup/11-2) are shown in the FIG. 4*a*. Similarly, rhabdomyosarcoma cells become enlarged, stop dividing, and also detach from the dish and die (control cells, FIG. 4*c*; cells suppressed by DNA superfragment 11sup/52-1, FIG. 4*d*). Thus, the tumor properties of multiple tumor cell types are eliminated by introduction of specific DNA superfragments.
5. FIG. 5 indicates the DNA that is present within the DNA superfragments that either do (80–100% of colony senescence) or do not abrogate the malignant phenotype. The DNA superfragments are first screened with a panel of genes throughout chromosome 11. Those hybrids containing 11p sequences are further analyzed in the present instance (Wilms tumor and rhabdomyosarcoma suppression), with ten gene probes, since 11p is thought to harbor a suppressor gene for these tumors. Each fragment is transferred to rhabdomyosarcoma cells (RD) and Wilms tumor cells (G401) via microcell fusion, as described above. The number of experiments varies from 1 to 3 for each fragment. The surviving colonies are identified after two weeks of selection in G418. At this time, non-treated parental cells die. For rhabdomyosarcoma cells, following 2–3 weeks, the number of cells in each colony is counted. If the number of cells descreases or stays the same during this period, the cells are considered to be senescent. For Wilms tumor cells, the cells grow to a large enough number for replating by trypsinization at this time, as described above. Trypsinized cells are transferred to 6 cm dishes in DMEM containing 10% FCS+G418 (400 μg/ml). For example, Wilms tumor cells which received the 11sup/52-1 superfragment grew about 20 population doublings ($10^6$ cells) and then stopped growing altogether. The suppressed cells also showed flat morphology. These cells were thus considered to show suppression. In contrast, cells which received 11sup/11-2 continued to grow unabated and could be subcultivated for at least 40–60 population doublings (the cells were not studied beyond this point). In addition, Wilms tumor cells that received 11sup/11-2 also continued to display the parental tumor morphology, unlike cells that received the suppressing superfragment 11sup/52-1. Eight different superfragments were transferred to rhabdomyosarcoma cells (RD), and 8 superfragments were transferred to Wilms tumor (G401). As described above, the suppressor phenotype was tested by observing colony size over time, as well as morphology. For RD cells, 6-17 colonies for each superfragment were tested (avg. 8), and for G401, 1-11 colonies were tested (avg. 7). Suppressing DNA superfragments caused morphological reversion to a nonmalignmant phenotype, as well as cessation of colony growth in 80% or more of the colonies.

As shown in FIG. 5, the portion of DNA that contains the tumor suppressor gene lies in a very small portion of DNA, isolated within a DNA superfragment, and near the globin gene on band 11p15. Occasionally, a superfragment is a combination of two smaller fragments, but that does not hinder expression of the phenotype (e.g., 52-1 has suppressor activity). Importantly, the region containing the suppressor gene is less than one million nucleotides in size, a reduction in complexity of approximately 130 over that of our starting reagent, the whole chromosome 11. It is a relatively straightforward task, using conventional technologies, to isolate the individual suppressor gene from this superfragment. Thus, the gap between whole chromosome complementation, which is not amenable to direct gene cloning, to DNA superfragments that are amenable to direct gene cloning has been bridged by the present invention. By isolating individual DNA superfragments that can be transferred to a given cell to screen for a given phenotype, it is now possible to identify with certainty the portion of the chromosome that contains that gene and, in a single stroke, to isolate that fragment from the remainder of the human genome. The fact that 11p15 is thought to harbor suppressor genes for several common malignancies, including bladder, breast, and lung cancer (I.U. Ali et al, *Science*, vol. 238, pp. 185–188 (1987); E.R. Fearon et al, *Nature*, vol. 309, pp. 176–178 (1984); and A. Weston et al, *Proc. Natl. Acad. Sci. USA*, vol. 86, pp. 5099–5103 (1989)) is particularly intriguing. Thus, since a suppressor gene now has been localized to 11p15, this DNA superfragment may also contain genes of great general medical importance. Obviously, the same strategy can be applied to other genes on chromosome 11 and other chromosomes, as well. Indeed, a total 85 DNA superfragments from throughout chromosome 11 have been isolated.

Mouse A9 cells containing human X;11 (named A9(X/11-1-1)), mouse A9 cells containing 11sup/74-1, mouse A9 cells containing 11sup/51-6, and mouse A9 cells containing 11sup/52-1 have all been deposited with the American Type Culture Collection, 12301 Parklawn Drive, Rockville, Md. 20852 USA. Accession numbers have not yet been assigned. All references cited in this application are incorporated herein by reference.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A method for forming a DNA superfragment, comprising:
   (i) irradiating microcells, which contain a chromosome that contains a first and a second marker, with γ-irradiation of a dosage of 1,000 to 100,000 rads.

2. The method of cloning a gene, comprising:
   (i) introducing a foreign chromosome, containing a first marker, into a host cell, wherein the genome of said host cell does not contain said first marker;
   (ii) introducing a second marker randomly in said foreign chromosome to obtain chromosomes which correspond to said foreign chromosome and contain both said first and said second marker;
   (iii) selecting for cells which contain chromosomes having said second marker to obtain a first cell culture which contains cells that contain chromosomes having said second marker, and which does not contain cells that do not contain chromosomes having said second marker;
   (iv) forming first microcells from cells of said first cell culture;
   (v) fusing said first microcells to first recipient cells, to obtain fused cells;
   (vi) culturing said fused cells to select for the presence of chromosomes which contain both said first marker and said second marker, to obtain a second cell culture, which contains cells that have a chromosome containing both said first and said second marker, and which does not contain cell that do not have a chromosome containing both said first and said second marker;
   (vii) forming second microcells from said second cell culture;
   (viii) irradiating said second microcells, with γ-irradiation, to obtain irradiated microcells;
   (ix) fusing said irradiated microcells with second recipient cells, to obtain second fused cells; and
   (x) culturing said second fused cells to select for the presence of a DNA fragment which contains said second marker, to obtain a third cell culture which contain cells that have a DNA fragment containing said second marker and which does not contain cells that do not have a DNA fragment containing said second marker.

3. A fragment of chromosomal DNA, which contains from 1 million to 100 million base pairs, which contains an exogenous selectable marker, and which contains a tumor suppressor gene.

4. The fragment of claim 3, which is selected from the group consisting of 11sup/74-1, 11sup/52-1, and 11sup/51-6.

5. A fragment of human chromosome 11 having from 1 million to 100 million base pairs and which contains an exogenous selectable marker.

6. The fragment of claim 5, wherein said fragment is selected from the group consisting of 11sup/74-1, 11sup/52-1, and 11sup/51-6.

* * * * *

UNITED STATES PATENT AND TRADEMARK OFFICE
CERTIFICATE OF CORRECTION

PATENT NO. : 5,240,840                     Page 1 of 2
DATED      : August 31, 1993
INVENTOR(S): Andrew P. Feinberg, et al It is certified that error appears in the above-indentified patent and that said Letters Patent is hereby corrected as shown below:

Column 1, Line 57, "base pairs A total" should read --base pairs. A total--

Column 2, Line 23, "Identification of the cystc fibrosis" should read --Identification of the cystic fibrosis--

Column 10, Line 63, "is not limited the abovedescribed example" should read --is not limited to the above-described example--

Column 11, Line 32, "A9 cells, but can by any" should be --A9 cells can be any--

Column 15, Line 7, "Fragmentation of Neo-tagged" should read --IV. Fragmentation of Neo-tagged--

Column 17, Line 1, "are label" should read --are labeled--

UNITED STATES PATENT AND TRADEMARK OFFICE
CERTIFICATE OF CORRECTION

PATENT NO. : 5,240,840
DATED : August 31, 1993
INVENTOR(S) : Andrew P. Feinberg, et al Page 2 of 2

It is certified that error appears in the above-indentified patent and that said Letters Patent is hereby corrected as shown below:

Column 17, Line 55, "and introduce then" should read --and introduce them--

Column 18, Line 7, "photographs ware" should read --photographs were--

Column 20, Line 39, "does not contain cell that" should read --does not contain cells that--

Signed and Sealed this

Fourth Day of April, 1995

Attest:

BRUCE LEHMAN

Attesting Officer

Commissioner of Patents and Trademarks